DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED JANUARY 26, 1971

882 O.G. 1345

T882,016

DIOL MONOETHERS AND THEIR MANUFACTURE

Frank C. Canter and Alfred G. Robinson III, both of P.O. Box 2068, Longview, Tex. 75601

Continuation of application Ser. No. 833,699, June 16, 1969, which is a continuation-in-part of application Ser. No. 511,350, Dec. 3, 1965. This application Apr. 9, 1970, Ser. No. 24,432

Int. Cl. C07c *43/00*

U.S. Cl. 260—615

No Drawing. 11 Pages Specification

Diol monoethers containing a neopentyl structure are prepared by the catalytic hydrogenation of certain cyclic diethers at elevated temperatures and pressures. Diol monoethers having a quaternary carbon atom are particularly useful, for example, as solvents, as high-temperature functional fluids or as intermediates for other useful chemical compounds such as plasticizers and wetting agents.